United States Patent [19]

de Couët et al.

[11] Patent Number: 4,781,678

[45] Date of Patent: Nov. 1, 1988

[54] SURGICAL DRAIN

[75] Inventors: Alexandre de Couët, Zürich, Switzerland; Mohamed Hamid, Schiltigheim, France

[73] Assignee: Imtec S.A., Zurich, Switzerland

[21] Appl. No.: 21,833

[22] Filed: Mar. 4, 1987

[30] Foreign Application Priority Data

Mar. 6, 1986 [FR] France .................. 86 03321

[51] Int. Cl.$^4$ .................................. A61M 3/00
[52] U.S. Cl. .................... 604/45; 604/266; 604/280
[58] Field of Search .............. 604/266, 267, 43–45, 604/93, 119, 280–284

[56] References Cited

U.S. PATENT DOCUMENTS

| | | | |
|---|---|---|---|
| 2,930,378 | 3/1960 | Buyers | 604/45 |
| 3,114,373 | 12/1963 | Anderson | 604/45 |
| 3,421,510 | 1/1969 | Kettenbach | 604/45 |
| 3,528,427 | 9/1970 | Sheridan et al. | 604/45 |
| 3,999,554 | 12/1976 | Kim et al. | 604/45 |

Primary Examiner—John D. Yasko
Attorney, Agent, or Firm—Sughrue, Mion, Zinn, Macpeak, and Seas

[57] ABSTRACT

The drain of this invention includes a tube provided with orifices for drawing in residual secretions gathered at the site of an operation. Within the tube is bounded a volume of variable capacity. Such volume is divided into one or several inflatable pockets bounded between the internal wall of the tube and a sleeve judiciously fastened to said wall. Such sleeve is of elastic material. A suction source is connected to the channel left free within the tube by the sleeve. Furthermore, a fluid source may be connected to the volume bounded by the sleeve to enable changing the capacity thereof. Such changes serve to unclog the intake orifices.

The invention is applicable to surgical drains used in the post-operational phase to remove all secretions appearing at the site of the operation.

13 Claims, 2 Drawing Sheets

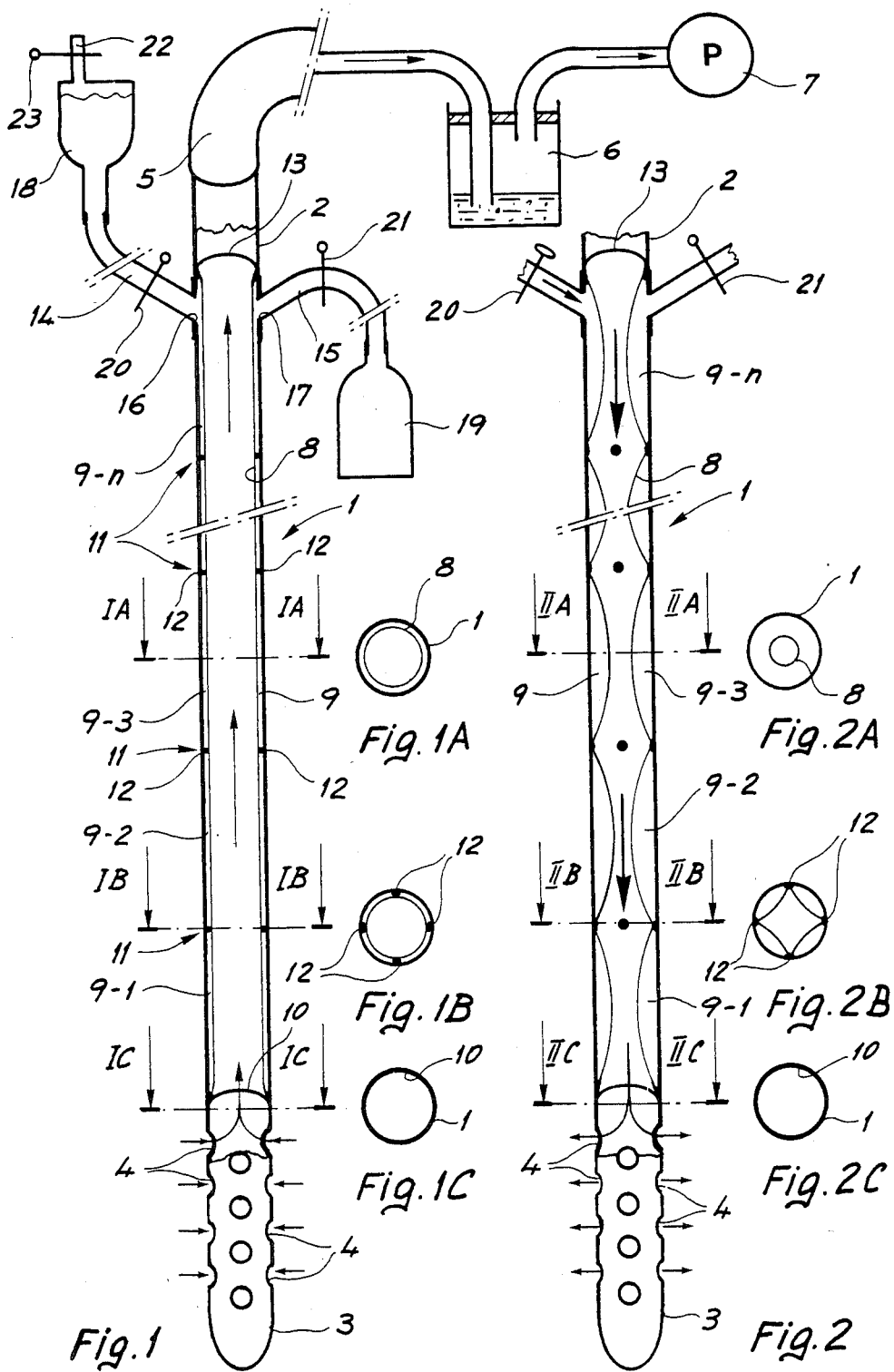

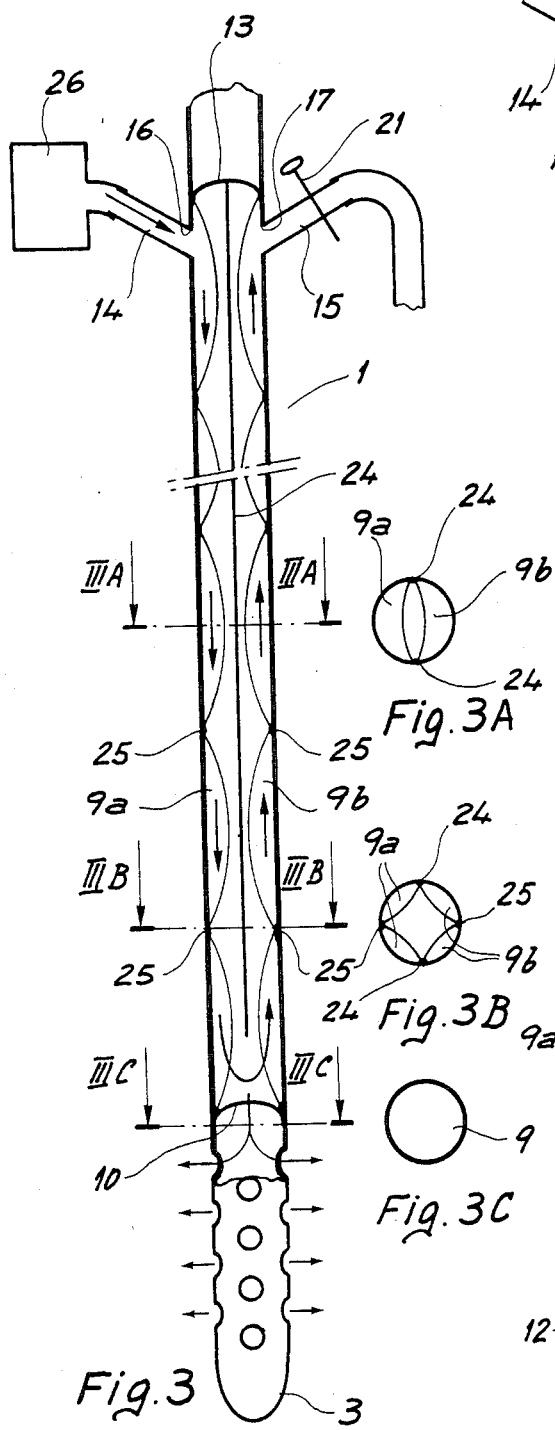
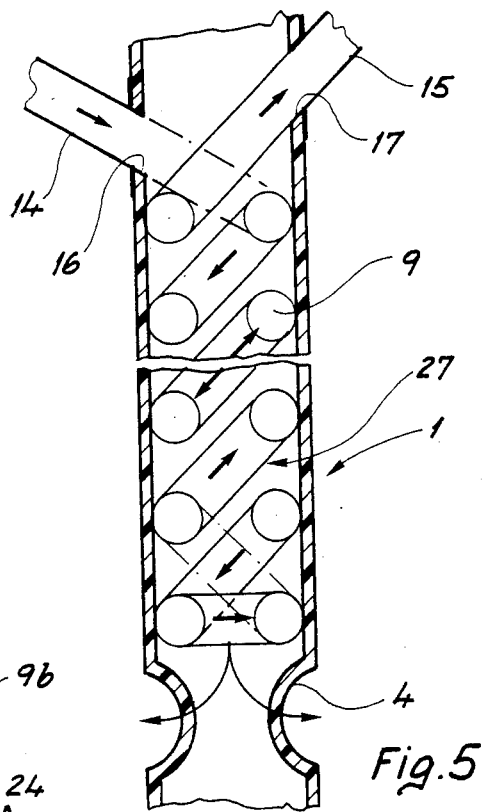
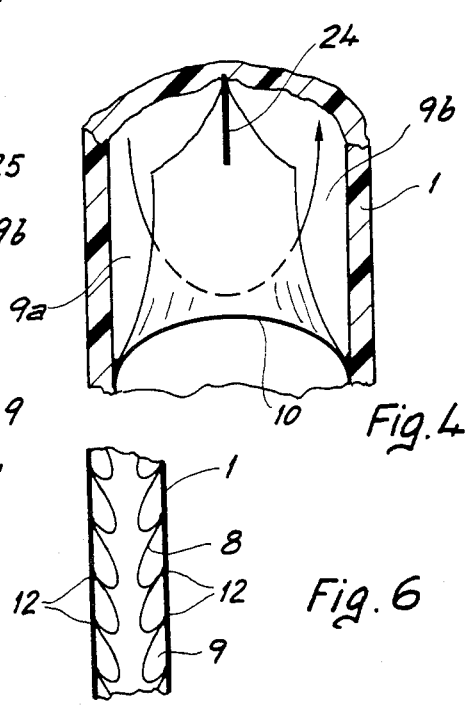

SURGICAL DRAIN

This invention concerns a surgical drain mainly employed during the post-operational phase for removing from the site of the operation any substance which may react unfavourably at this site.

In particular, the ideal and fundamental function of all draining consists of removing to outside the abdominal, thoracic or pelvic cavities:

(a) all collections susceptible of being formed after a surgical operation;

(b) all serious haemorrhage or secretion in order that the surgeon may rapidly reoperate since the drain left in the surgical site constitutes a valve signalling any complication;

(c) all abnormal leakage of organic substances, the removal of which spares organs proximate the surgical site, in particular if such substances should be corrosive or likely to cause infection.

BACKGROUND OF THE INVENTION

At present the majority of known surgical drains have a tendency to become blocked during a period varying between some minutes and several hours following their installation, according to the anatomical regions and the viscosity of the substances which are to be removed by the drain. It is evident that this obstruction is troublesome since it blocks the functions which have been mentioned hereinabove. The avoidance of such obstruction is thus a constant preoccupation of medical practitioners.

Within the special field of the abdominal, thoracic or pelvic cavity, an obstruction may be produced in three different manners:

since the intra-abdominal, intra-thoracic or intrapelvic organs have a certain physiological mobility, they come into contact with the drain so as to stick to it, and this to a proportionally greater extent if the drain is more frequently subjected to suction to stimulate the removal of the fluids;

the drained substances have a viscosity becoming greater and greater, in particular because of the coagulation and they adhere thus more and more to the internal wall of the drain and end up by blocking it;

by its implantation the inclination of the drain is often not favourable, in particular because of the prone position of the patient. In this case the drain does not benefit from any slope and gravity annuls the syphon effect.

An attempt to provide a drain enabling avoidance of this mediocre operation of well-known drains has been described in the U.S. Pat. No. 3,114,373. In this case there is disclosed a drain set comprising a main tube closed at its distal end and connected to a suction source at its proximal end. The distal end placed within the cavity to be drained (here the gastro-intestinal space) is provided with a row of orifices opening laterally from the tube and through which are drawn in the substances to be removed.

This main tube is flanked by an auxiliary tube which opens out into the main tube entirely at its closed distal end, i.e. beyond the evacuation orifices. At its other end, the auxiliary tube may be left open to the atmosphere, connected to a hypodermic source or to another medication source, or to a bottle containing a saline solution. Air and/or the saline solution may thus flow continuously through the auxiliary tube into the space bounded by the distal end of the main tube in order to be mixed with the drained substances and thus avoid the clogging and deterioration of neighbouring tissues while maintaining within the drain a sufficient air flow.

If the saline solution may to a certain extent avoid coagulation and dissolve the conglomerates forming in the evacuation tube, these difficulties are not avoided if air in place of this solution is introduced into the auxiliary tube. The necessity of a saline solution complicates considerably the drain itself and its employment since the overseeing personnel must renew it, prepare it or obtain it, etc. Furthermore, the saline solution may not be tolerated by the organs surrounding the drain.

On the other hand, in the case of employment on a surgical site, it is out of the question to send ambient air as such into the auxiliary tube since it would be coming from a non-sterile medium. It will thus be necessary to provide an arrangement for sterilizing air or otherwise a source of sterile air which still further complicates the matter, particularly the installation and employment thereof.

The invention has thus as purpose to provide an improved surgical drain which avoids these difficulties and assures permanently the existence of a drain passage without risk of obstruction thereof by coagulation, solid residues or surrounding organs.

SUMMARY OF THE INVENTION

The invention thus provides a surgical drain for the evacuation in a post-operational phase of all harmful secretions appearing at a surgical site including a tube the distal end of which is closed and provided with lateral orifices for drawing in said secretions and the proximal end of which is arranged to be connected to a vacuum source, said tube having associated therewith a duct arrangement intended to hold a fluid apt to avoid blocking of said orifices while said drain is in use, such duct arrangement being bounded between the inner wall of the tube and a sleeve of elastic material fastened within said tube in a manner arranged to provide in the latter a volume of selectively variable capacity and formed by at least one pocket communicating with a fluid source but separated from the passage left free within the tube for removal of the secretions, said fluid being able to be introduced and extracted from said pocket in order to enable the expansion and contraction thereof.

Thus, thanks to the invention, the orifices of the drainage tube may be periodically unclogged, either automatically, for example by pulsation of the dilating fluid or manually by sending said fluid into a pocket in accordance with the needs as determined by the overseeing personnel.

BRIEF DESCRIPTION OF THE DRAWINGS

FIG. 1 is a schematic view of a drain arrangement comprising the drain in accordance with the invention;

FIGS. 1A, 1B and C are transversal cross-sections of the drain of FIG. 1;

FIG. 2 is a view analogous to that of figure 1 wherein the pockets of the drain are dilated;

FIGS. 2A, 2B and 2C are cross-sections of the drain of FIG. 2;

FIG. 3 shows schematically another embodiment of the drain in accordance with the invention;

FIGS. 3A, 3B and 3C are cross-sections of the drain of FIG. 3;

FIG. 4 is a partial view to an enlarged scale of a part of the drain of FIG. 3;

FIG. 5 shows another embodiment of the invention;
FIG. 6 shows a variant of the invention.

DESCRIPTION OF THE PREFERRED EMBODIMENT

FIGS. 1 to 2C represent a first embodiment of the invention. In this example the drain includes a tube 1 having a proximal end 2 and a distal end 3. To give an idea of the scale, tube 1 may have a total length of 20 to 30 cm. It is closed at its distal end, close to which are provided orifices 4 bringing about coommunication of the interior of tube 1 with the exterior, i.e. with a cavity of the human body when the tube is placed therein following a surgical operation within the cavity in question. One may provide several ranks of holes spread apart from one another by 90°, the ranks being staggered according to the longitudinal direction, and from 3 to 5 holes per rank being foreseeable.

The proximal end 2 of the tube is connected to pipe 5 through which the substances to be removed from the cavity are drawn towards a container 6 which is under vacuum or, as shown, is connected to a suction pump 7.

The inner wall of the tube 1 is lined with a sleeve 8 of elastic material such as polyvinyl chloride, weldable to the tube material which may likewise be formed of a vinyl material, of "Silastic" or rubber. However, tube 1 is preferably formed from a material having a certain rigidity.

Sleeve 8 bounds a volume 9 within tube 1 which is separated from the interior of the latter and which extends over the entire length thereof with the exception of a zone in which are pierced orifices 4.

The sleeve 8 may be fastened to the interior of the tube 1 in the following manner. Just above orifices 4 it is fixed over its entire periphery to the wall of the tube 1 to form a sleeve closing circle 10. Between this closing circle 10 and the proximal end 2 of tube 1 the sleeve is fixed at points 12 to the inner wall of the latter within fastening zones 11. Then at its upper end the sleeve 8 is again fixed over its entire periphery to the wall of tube 1 forming another closing circle 13. Thus, between the wall of tube 1 and the sleeve 8 there are formed several pockets 9-1, 9-2, 9-n forming together volume 9. The closing circles 10 and 13 as well as points 12 may be obtained by welding, by gluing or by any other appropriate fastening means.

At the same time it should be noted that volume 9 may likewise be continuous in order to form a single annular pocket extending between the closing circles 10 and 13. It is well understood in this variant, that the fastening points 12 are unnecessary.

Just below closing circle 13 opening into the volume 9 are two necks 14 and 15 through respective orifices 16 and 17 provided in the wall of tube 1. In the embodiment shown, necks 14 and 15 are connected respectively to containers 18 and 19.

Stopcocks 20 and 21 are inserted in the necks 14 and 15. On the drawing, each of these stopcocks is symbolically shown by a line arranged across the channel in which it is inserted, it being understood that it is closed when its handle is shown by a circle and open when this handle is symbolized by an oval. It is to be noted that the material (stopcocks, tubes, containers, etc.) which has just been described, may readily be found in commerce since it is currently employed for perfusions, for instance.

In the configuration of FIG. 1, it is supposed that the drain in accordance with the invention has just been put into place following a surgical operation and that the containers 18 and 19 are connected as well as container 6 and the vacuum pump 7. Stopcocks 14 and 15 are in their closed position while container 18 is filled with a dilating fluid such as non-sterile water, for instance. The container 18 provides furthermore a vent 22 which is provided with a stockcock 23 to permit selective communication of the container 18 with ambient air.

Some time following its installation, the drain may become obstructed for reasons as set out hereinabove. The nursing personnel then proceeds to expanding volume 9 in the following manner. Stopcocks 20 and 23 are opened, thus causing water to flow into volume 9. Sleeve 8 being supple, hydrostatic pressure dilates it and thus suddenly reduces the interior volume of tube 1. There results therefrom an increase of pressure at the distal end of the drain which acts on tissues which may have blocked the orifices 4 in order to remove such therefrom. Simultaneously, the secretions higher up in the drain are retained by the barriers successively formed from bottom to top by the pocket or pockets which the sleeve has formed when it is dilated. Thus the progressive expansion of the pocket or pockets forming volume 9 brings about a snaking movement from bottom to top tending to eject the secretions and above all material susceptible of coagulation or of adhering to the walls formed by sleeve 8. It is noted thus that the drain in some manner constitutes an imitation of a vein and of its valvules.

To bring about contraction of volume 9, it is sufficient to close stopcock 20 and open stopcock 21 so as to enable the water to flow from the volume 9 into container 19. Such operation may be facilitated by using for this latter a container previously put under vacuum.

The nursing personnel may repeat as often as necessary the cycle which has just been described, at moments more or less spaced out over time.

It is noted that at no time can the expansion fluid communicate with the interior of the drain itself, the volume 9 being perfectly isolated therefrom. In this manner the expansion fluid has no need to be sterile.

FIGS. 3 to 3C and 4 represent a variant of the invention which differs from the embodiment of the preceding figures only by the fact that the sleeve 9 is attached to the inner wall of the tube by two diametrally opposed longitudinal lines of welding 24 and from space to space by welding points 25, likewise diametrally opposed, but spread apart by 90° relative to the welding lines 24. At the top and at the bottom the sleeve 8 is fixed to the wall of the tube 1 by closing circles 10 and 13 as in the previous embodiment. In these conditions the volume bounded between the wall of tube 1 and the sleeve 8 is formed by two longitudinal chambers 9a and 9b which do not communicate with one another except close to the closing circle 10.

In this variant it is supposed furthermore that the neck 14 is connected to a pumping arrangement 26 capable of effecting a periodically variable pressure of the dilating fluid with which volume 9 is filled. It may for instance be an apparatus of the type "Vial Medical" (registered trademark) type SE200. This apparatus is conceived in a manner such that a syringe of standard form may there be maintained thereto while the piston thereof may be operated in a programmable fashion by a movable push-piece. The operating program may be chosen in accordance with needs (intermittent operation with determination of the period between two operations, etc.).

The employment of such a pumping arrangement presents the advantage of being adapted to remain permanently connected to the drain without it being necessary that the personnel intervene regularly. As already indicated, the frequency of the pressure variation may be regulated as well as the average value of this pressure. As is well understood, the embodiment of FIGS. 1 to 2C may likewise be provided with an automatic pumping arrangement such as arrangement 26.

FIG. 5 shows yet another variant of the invention in which the volume 9 is bounded by a single pocketk formed by a second tube 27 wound up in two interlaced helices communicating with one another at the distal end of the drain and opening at the proximal end respectively into necks 14 and 15. This tube is likewise formed of elastic material in a manner to be capable of expansion and contraction according to needs.

The dilating fluid may be water, air, oxygen or any other appropriate fluid. There is no need for it to be sterilized. If the suction pressure required for the removal of the secretions is chosen to be between 15 and 20 mm Hg for instance, an expansion pressure for volume 9 may be from 15 to 20 mm Hg likewise. However, suction pressures situated between 8 and 30 mm Hg may also be envisaged.

It may further be noted that a judicious choice of the locations for the fastening points of sleeve 8 enables forming types of small compartments (FIG. 6). Thus, in the contracted configuration, the length of sleeve 8 between two fastening points may be greater than the length of the tube between those two points. Otherwise the longitudinal distance between two fastening points may be less than that shown on the drawings.

What we claim is:

1. A surgical drain for the evacuation in a post-operational phase of harmful secretions appearing at a surgical site, said surgical drain comprising:
    a tube having a sustantially closed distal end, at least one lateral orifice provided in close proximity of said distal end, and an open proximal end,
    said open proximal end being adapted for having suction applied thereto,
    an elastically deformable, substantially sleeve-shaped member, extending substantially coaxially through said tube and defining therein a central passage way communicating with said open proximal end and said lateral orifice, said sleeve-shaped member being fastened in a fluid tight manner to the inner wall of said tube, at least at locations which are respectively close to said proximal end and to said orifice whereby said sleeve shaped member defines with said inner wall of said tube at least one inflatable pocket sealed off with respect to said passage way, and means for selectively supplying pressure medium to said at least one pocket to selectively inflate the same, thereby modifying the overall volume of said central passage way defined by said sleeve shaped member.

2. A surgical drain as set forth in claim 1 wherein said sleeve-shaped member is fastened to the inner wall of the tube at points spaced apart in such a manner as to define with said inner wall of said tube a plurality of pockets communicating with one another.

3. A surgical drain as set forth in claim 2 wherein said sleeve-shaped member is also fastened to said inner wall of said tube along two generating lines which are diametrally opposed except within a zone located in close proximity of the distal end of said sleeve-shaped member.

4. A surgical drain set forth in claim 2 wherein the length of a portion of said sleeve-shaped member situated between two adjacent longitudinally spaced fastening points is greater than the corresponding length of the tube between such points.

5. A surgical drain as set forth in claim 1 wherein said means for selectively supplying pressure medium to said at least one pocket comprises input port means provided in said wall of said tube and communicating with said at least one pocket, said input port means comprising valve means for selectively opening and closing said input port means.

6. A surgical drain as set forth in claim 5 wherein said means for selectively supplying pressure medium to said at least one pocket further comprises output port means provided in said wall of said tube and communicating with said at least one pocket, said output port means comprising valve means for selectively opening and closing said output port means.

7. A surgical drain as set forth in claim 5 wherein said input port means is located is close proximity to said proximal end of said tube.

8. A surgical drain as set forth in claim 6 wherein said input port means and said output port means are located in close proximity to said proximal end of said tube.

9. A surgical drain for the evacuation in a post-operational phase of harmful secretions appearing at a surgical site, said surgical drain comprising:
    a tube having a substantially closed distal end, at least one lateral orifice provided in close proximity of said distal end, and an open proximal end,
    said open proximal end being adapted for having suction applied thereto,
    an elastically deformable inflatable member comprising two interlaced coaxial pipe helices inserted coaxially in said tube and fastened to the inner wall thereof, said coaxial pipe helices being in mutual fluid communication at the distal end of said tube in close proximity to said at least one lateral orifice;
    input port means provided in said wall of said tube and in fluid communication with one of said coaxial pipe helices.
    and valve means associated with said input means for selectively supplying pressure medium through said input port means to said coaxial pipe helices.

10. In combination:
(i) a surgical drain for the evacuation in a post-operational phase of harmful secretions appearing at a surgical site, said surgical drain comprising:
    a tube having a substantially closed distal end, at least one lateral orifice provided in close proximity of said distal end, and an open proximal end,
    said open proximal end being adapted for having suction applied thereto,
    an elastically deformable, substantially sleeve-shaped member, extending substantially coaxially through said tube and defining therein a central passage way communicating with said open proximal end and said lateral orifice, said sleeve-shaped member being fastened in a fluid-tight manner to the inner wall of said tube, at least at locations which are respectively close to said proximal end and to said orifice, whereby said sleeve-shaped member defines with said inner wall of said tube at least one inflatable pocket sealed off with respect to said passage way, and means for selectively supplying pressure medium to said at least one pocket to selectively inflate the same, thereby modifying the overall volume of said central passage way defined by said sleeve-shaped member, (ii) a first vessel in fluid communication with said proximal end of said tube for receiving the harmful secretions removed from said site through said passage way, (iii) a vacuum source in fluid communication with said first vessel, (iiii) said means for selectively supplying pressure medium to said at least one pocket comprising a second vessel which contains said pressure medium and is in fluid communication with said at least one pocket.

11. The combination as set forth in claim 10 further comprising a third vessel which is in fluid communication with said at least one pocket for selectively receiving said pressure medium from said at least one pocket.

12. A surgical drain as set forth in claim 10 wherein said pressure medium is pulsed.

13. A surgical drain as set forth in claim 10 wherein said pressure medium comprises air, oxygen or water

* * * * *